United States Patent [19]
Plöger et al.

[11] 3,960,888
[45] June 1, 1976

[54] PYRROLIDONE-5,5-DIPHOSPHONIC ACIDS

[75] Inventors: Walter Plöger, Hilden Rhineland; Manfred Schmidt-Dunker, Dusseldorf; Christian Gloxhuber, Haan Rhineland, all of Germany

[73] Assignee: Henkel & Cie G.m.b.H., Dusseldorf-Holthausen, Germany

[22] Filed: Aug. 20, 1974

[21] Appl. No.: 498,997

[30] Foreign Application Priority Data
Aug. 27, 1973  Germany............................ 2343147

[52] U.S. Cl..................... 260/326.5 A; 252/49.9; 252/175; 252/381; 260/326.5 FN; 423/555; 424/DIG. 6; 424/49; 424/200
[51] Int. Cl.²............................. C07D 207/24
[58] Field of Search............ 260/326.5 A, 326.5 FN, 260/502.5

[56] References Cited
UNITED STATES PATENTS

| | | | |
|---|---|---|---|
| 2,644,002 | 6/1953 | Hoegberg...................... | 260/326.5 A |
| 2,706,194 | 4/1955 | Morris et al. ............ | 260/326.5 A X |
| 2,844,582 | 7/1958 | Raley, Jr.................. | 260/326.5 A X |
| 2,865,912 | 12/1958 | Pohlemann et al. ...... | 260/326.5 A X |
| 2,902,493 | 9/1959 | Lorenz et al................. | 260/326.5 A |
| 3,448,118 | 6/1969 | Chickery et al. .......... | 260/326.5 FN |
| 3,846,420 | 11/1974 | Wollmann et al. .............. | 260/502.5 |

*Primary Examiner*—Dale R. Ore
*Attorney, Agent, or Firm*—Hammond & Littell

[57] ABSTRACT

Pyrrolidone-5,5-diphosphonic acids having the formula

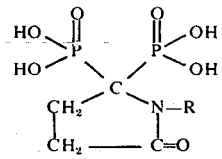

wherein R is a member selected from the group consisting of hydrogen and alkyl having from 1 to 6 carbon atoms; as well as their water-soluble salts. The pyrrolidone-5,5-diphosphonic acids are excellent sequestering agents especially for alkaline earth metal ions. They are stabilizers for percompounds and are useful in the delaying of the setting times for gypsum. In addition, the compounds are useful as cosmetic preparations such as toothpastes and mouthwashes where they prevent formation of tartar and plaque and are useful in therapy in the treatment of diseases related to the abnormal deposition or dissolution of difficultly soluble calcium salts in the animal body.

9 Claims, No Drawings

PYRROLIDONE-5,5-DIPHOSPHONIC ACIDS

OBJECTS OF THE INVENTION

An object of the present invention is the obtaining of a pyrrolidone-5,5-diphosphonic acid derivative selected from the group consisting of (1) compounds of the formula

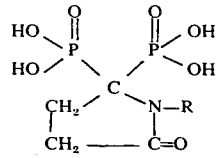

wherein R is a member selected from the group consisting of hydrogen and alkyl having from 1 to 6 carbon atoms, and (2) water-soluble salts thereof.

Another object of the present invention is the development of a process for the production of the above pyrrolidone-5,5-diphosphonic acids or their water-soluble salts.

Another object of the present invention is the development of a process for the delaying or inhibiting of the precipitation of alkaline earth metal ions from solution by the use of stoichiometric to substoichiometric amounts of the above pyrrolidone-5,5-diphosphonic acids or their water-soluble salts.

A further object of the present invention is the development of a method for delaying the setting time for gypsum which comprises adding to the mixture of plaster materials and water a small amount of the above pyrrolidone-5,5-diphosphonic acids or their water-soluble salts.

A yet further object of the present invention is the development of a method for the treatment of diseases related to the abnormal deposition or dissolution of difficultly soluble calcium salts which comprises administering a safe but effective amount of at least one of the above pyrrolidone-5,5-diphosphonic acids or their water-soluble salts to the warm-blooded animal.

These and other objects of the invention will become more apparent as the description thereof proceeds.

DESCRIPTION OF THE INVENTION

The above objects have been achieved by the development of new pyrrolidone-5,5-diphosphonic acid derivatives selected from the group consisting of (1) compounds of the Formula I

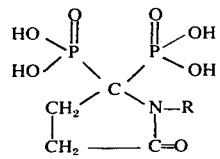

(I)

wherein R is a member selected from the group consisting of hydrogen and alkyl having from 1 to 6 carbon atoms, preferably alkyl having 1 to 4 carbon atoms, and (2) water-soluble salts thereof; as well as a process for the manufacture of the new compounds and their applications.

The production of the new pyrrolidone -5,5-diphosphonic acids or their water-soluble salts can occur by the reaction of a suitable derivative of succinic acid with a phosphorus trihalide or phosphorous acid and a phosphorus trihalide and subsequent alkaline hydrolysis of the reaction product. In general, the reactions are conducted at temperatures between 50°C and 120°C. The suitable derivatives of succinic acid are succinic acid dinitrile and succinic acid diamide. In addition, succinic acid diamides may be employed in which one hydrogen atom in each amido group was replaced by an alkyl having from 1 to 6 carbon atoms.

The reaction can be carried out, for example, in that the above-mentioned succinic acid derivatives are melted with phosphorous acid, and then $PCl_3$ is slowly added while stirring. The reaction product formed is subsequently subjected to alkaline hydrolysis. This can be done by boiling with aqueous solutions of strong bases, particularly with sodium hydroxide or potassium hydroxide solutions.

The above process can also be conducted by starting from succinic acid dinitrile dissolved in an inert solvent such as dioxane or chlorinated hydrocarbons, and subsequently mixed with phosphorus trihalide. Then phosphorous acid, preferably dissolved in an inert solvent, is added and the reaction product is hydrolyzed as above. In the last mentioned method, the phosphorous acid can also be omitted, if desired, and a correspondingly larger amount of phosphorus trihalide employed.

More particularly, the above process for the production of the new pyrrolidone-5,5-diphosphonic acid derivatives of Formula I consists essentially of the steps of reacting a derivative of succinic acid of the formula

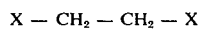

wherein X is a member selected from the group consisting of —CN, —$CONH_2$ and —CONHR', where R' is alkyl having 1 to 6 carbon atoms, with at least the stoichiometric amount of a phosphorus reactant selected from the group consisting of a phosphorus trihalide and a mixture of a phosphorus trihalide and phosphorous acid, subjecting the resulting reaction product to an alkaline hydrolysis by the action of an aqueous strong mineral base, and recovering said pyrrolidone-5,5-diphosphonic acid derivative.

The new pyrrolidone-5,5-diphosphonic acid derivatives of Formula I can also be produced by reacting a succinic acid monoamide or succinimide in the above described manner with phosphorus trihalides or phosphorous acid and phosphorus trihalides, and the reaction product is subsequently hydrolyzed. In this case, it is not necessary to use an alkaline hydrolysis. The hydrolysis can be effected by adding water with simultaneous heating.

More particularly the above process for the production of the new pyrrolidone-5,5-diphosphonic acid derivatives of Formula I consists essentially of the steps of reacting a derivative of succinic acid selected from the group consisting of a compound of the formula

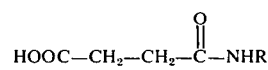

and a compound of the formula

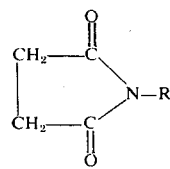

wherein R is a member selected from the group consisting of hydrogen and alkyl having 1 to 6 carbon atoms, with at least the stoichiometric amount of a phosphorus reactant selected from the group consisting of a phosphorus trihalide and a mixture of a phosphorus trihalide and phosphorous acid, subjecting the resulting reaction product to an aqueous hydrolysis at an elevated temperature, and recovering said pyrrolidone-5,5-diphosphonic acid derivative.

In the above reactions the phosphorus trihalides which can be used are particularly phosphorus trichloride and phosphorus tribromide. The latter was found to be particularly suitable, if the nitriles are employed as the starting material.

The molar quantitative ratio of the succinic acid derivatives to the phosphorus reactant is 1:2 to 1:6. If succinic acid dinitrile or succinic acid diamides are used, a ratio of 1:4 is preferably utilized.

As far as the pyrrolidone-5,5-diphosphonic acids are obtained after an alkaline hydrolysis, they are obtained in the form of the corresponding alkali metal salts. They can be converted, if desired, according to known methods into the corresponding free acids, for example, by means of cation-exchangers. For the uses described below, however, the new pyrrolidone-5,5-diphosphonic acid derivatives can be also used in the form of their water-soluble salts, particularly the alkali metal salts, such as the potassium and sodium salts, and ammonium salts. Insofar as the pyrrolidone-5,5-diphosphonic acid derivatives are obtained directly in the form of the acids, they can be easily converted into the water-soluble salts, for example, by partial or complete neutralization with corresponding bases.

The salts correspond to the following Formula Ia

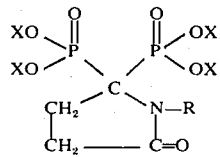

(Ia)

where X denotes hydrogen, $NH_4$ or a metal cation, such as an alkali metal, but where at most three hydrogen atoms are present, R = hydrogen or alkyl with 1 to 6, preferably 1 to 4 carbon atoms.

Finally it was found that the pyrrolidone-5,5-diphosphonic acid derivatives of the Formula I can also be produced by alkaline hydrolyzation of the phosphonic acids of the Formula II

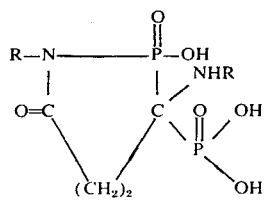

(II)

wherein R is hydrogen or alkyl having 1 to 6 carbon atoms. By following this method the new pyrrolidone-5,5-diphosphonic acid derivatives of Formula I are obtained in particularly good yields. The salts obtained can then be converted, if desired, in known manner into the corresponding acids, for example, by means of cation-exchangers.

The production of the compounds of Formula II can be effected by reacting dicarboxylic acid derivatives of the formula

$$X - (CH_2)_2 - X$$

where X = CN, $CONH_2$ or CONHR (R = alkyl radical with 1 to 6 carbon atoms), with phosphorus trihalides and subsequent hydrolyzation of the reaction product, as described in our copending patent application Ser. No. 498,996, filed concurrently herewith, entitled "Cyclic Aminophosphonic Acids".

It was analytically determined that the products from all the above-described production methods correspond to the cyclic Formula I and that possible products of the open-chained structure of Formula III

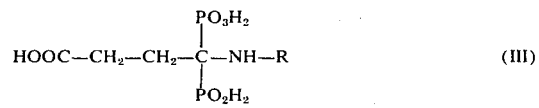

(III)

where R denotes hydrogen or alkyl with 1 to 6 carbon atoms, appear only in insignificant amounts.

The new pyrrolidone-5,5-diphosphonic acid derivatives are excellent sequestering agents for polyvalent metal ions, particularly di- and tri-valent metal ions. They are particularly suitable as sequestering agents for alkaline earth metal ions, so that they can be used for many technical applications, such as detergents and cleansers, as well as in water treatment. They can be employed in stoichiometric and substoichiometric amounts as sequestering agents for alkaline earth metal ions. They also have a stabilizing effect on percompounds.

They are also suitable as additives to delay the setting of gypsum and as ceramic slip liquefiers. For delaying the setting of gypsum, the potassium, sodium or ammonium salts, in addition to the acids, can also be used. The corresponding lithium salts as well as zinc and magnesium salts are likewise suitable.

Furthermore, they can be used in mouth washes and tooth pastes in order to avoid the formation of tartar or plaque. The suitability of the cyclic aminophosphonic acids to be used according to the invention for tartar treatment and prophylaxis, results from their capacity of inhibiting the formation of crystals in the precipitation of calcium apatite already in small amounts. Calcium apatite, which is precipitated in the presence of the pyrrolidone-5,5-dihosphonic derivatives, according to the invention, is X-ray amorphous, in contrast to crystalline apatite, which is usually formed without this addition.

The new pyrrolidone-5,5-diphosphonic acids and their water-soluble alkali metal and ammonium salts are suitable as pharmacological active substances in pharmaceutical products. They have therapeutic and/or prophylactic effects in the treatment of a number of diseases, which are related to the abnormal deposition or dissolution of difficultly soluble calcium salts in the animal body. These diseases can be divided into two categories:

1. Abnormal depositions of difficultly soluble calcium salts, mostly calcium phosphate, cause bone malformations, pathological hardening of tissues and secretions in organs.
2. The abnormal dissolution of hard tissues causes losses of hard bone substance, which cannot be replaced or only by incompletely crystallized tissue. This dissolution is frequently accompanied by pathologically high calcium and phosphate concentrations in the plasma.

These diseases include: osteoporosis, osteodystrophy, Paget's disease, myositis ossificans, Bechterew's disease, cholelithiasis, nephrolithiasis, urinary calculus, hardening of the arteries (sclerosis), arthritis, bursitis, neuritis, tetany.

In addition to the free pyrrolidone-5,5-diphosphonic acids, their pharmacologically harmless salts, such as the alkali metal salts, for example, sodium or potassium or the ammonium salts or the substituted ammonium salts, such as the lower alkanol ammonium salts like the mono-, di-, or triethanol ammonium salts can be used, for use in pharmaceutical preparations in the treatment of these diseases or for their prophylaxis. Both the partial salts, in which only a part of the acid protons are replaced by other cations, and full salts can be used, but partial salts, which react substantially neutral in aqueous solution (pH 5 to 9) are preferred. Mixtures of the above-mentioned salts can likewise be used.

The dosage range of the pyrrolidone-5,5-diphosphonic acid derivatives can be from 0.05 to 500 mg per kg of the animal body weight. The preferred dose is 1 to 20 mg per kg of body weight, and can be administered up to 4 times daily. The higher doses are necessary for oral application, due to the limited resorption. Doses under 0.05 per kg of body weight have little effect on the pathological calcification or dissolution of bone substance. Doses above 500 mg/kg of body weight may have toxic side effects in the long run. The pyrrolidone-5,5-diphosphonic acid derivatives can be administered orally, subcutaneously or intraperitoneally in the form of tablets, pills, capsules or as injectable solutions. For animals the pyrrolidone-5,5-diphosphonic acid derivatives can also be used as part of the feed or of feed additives.

The following examples are illustrative of the practice of the invention without being limitative thereof in any respect.

EXAMPLE 1

Pyrrolidone-5,5-diphosphonic acid

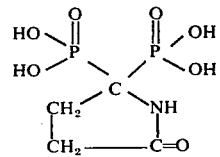

a. 24.4 gm of 2-hydroxy-2-oxo-3-amino-3-phosphonyl-6-oxo-1-aza-2-phosphacyclohexane (see Formula II) (0.12 mol) were heated with 400 ml of 2N sodium hydroxide solution to the boiling point for a period of time until no further ammonia escapes with the steam. The solution was then concentrated to 100 ml and mixed with 300 ml of ethanol. The precipitation of the sodium salt of the pyrrolidone-5,5-diphosphonic acid was completed with acetone and ethyl acetate. The oily substance was separated, dissolved again in $H_2O$ and passed through a cation exchanger in the hydrogen cycle. The solution obtained was concentrated to 100 ml, and the pyrrolidone-5,5-diphosphonic acid was precipitated with 300 ml of ethanol, 200 ml of acetone, and 200 ml of ethyl acetate. Yield 14.3 gm = 63% of the theory.

b. 58.5 gm of succinic acid monoamide (0.5 mol) and 41 gm of $H_3PO_3$ (0.5 mol) were melted at 70°C and mixed slowly with stirring with 43.8 ml of $PCl_3$ (0.5 mol). After 3 hours at 70°C the product was hydrolyzed with 200 ml of $H_2O$ and boiled with activated carbon. The hot solution was filtered and the pyrrolidone-5,5-diphosphonic acid was precipitated from the filtrate with 400 ml of ethanol and 400 ml of acetone. Crude yield 5.0 gm $\triangleq$ 3.8% of the theory.

c. 49.5 gm of succinimide (0.5 mol) and 41 gm of $H_3PO_3$ (0.5 mol) were heated to 70°C. To the homogeneous melt, 43.8 ml of $PCl_3$ (0.5 mol) were added slowly in drops. The reaction product was held for 4 hours at 70°C and then hydrolyzed with 200 ml of $H_2O$ as (b) above. The pyrrolidone-5,5-diphosphonic acid was precipitated from the filtrate with 300 ml of ethanol and 300 ml of acetone. Crude yield 4.6 gm = 3.5% of the theory.

d. 40 gm of succinic acid dinitrile (0.5 mol) were dissolved in 400 ml of dioxane and 190 ml of $PBr_3$ were added slowly in drops. After stirring for another 4 hours at 70°C the viscous yellow mass was hydrolyzed with 300 ml of water. After filtration with activated carbon, the dioxane was separated. The aqueous phase was mixed with 500 ml of 6N NaOH and heated until no further ammonia escaped. By adding an ethanol/acetone mixture, the sodium salt of pyrrolidone-5,5-diphosphonic acid was precipitated.

The free pyrrolidone-5,5-diphosphonic acid according to (a) to (c) was obtained after drying at 50°C as a monohydrate with a titrimetrically determined molecular weight of 265 (calc. 263.1). On drying at 80°C in a vacuum oven, the anhydrous compound was obtained with a molecular weight of 247 (calc. 245.07).

Analysis: Calculated: 19.60%, C; 3.70%, H; 5.71%, N; 25.28%, P. Found: 19.34, C; 3.61, H; 5.66, N; 25.24, P.

In the IR-spectrum the compound showed a strong $\nu CO$ band at 1610 $cm^{-1}$, M.P. 250°C with decomposition.

EXAMPLE 2

N-methyl-pyrrolidone-5,5-diphosphonic acid

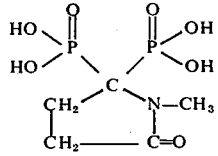

a. 64.4 gm of 1-methyl-2-hydroxy-2-oxo-3-methylamino-3-phosphonyl-6-oxo-1-aza-2-phospha-cyclohexane (0.237 mol) were heated with 800 ml of a 2N KOH solution to the boiling point for a period of time until no further methylamine passes over with steam. After filtration, the potassium salt of N-methyl-pyrrolidone-5,5-diphosphonic acid was separated from the alkaline solution by precipitation with ethanol and acetone. The potassium salt was again dissolved in $H_2O$ and passed through a cation exchanger in the hydrogen cycle. The N-methyl-pyrrolidone-5,5-diphosphonic acid was isolated from the concentrated solution with ethanol and acetone. Yield 16.4 gm (27% of the theory).

b. 28.5 gm of succinic acid monomethylamide (0.216 mol) were melted with 35.4 gm of $H_3PO_3$ (0.432 mol) at 70°C and then slowly mixed with 37.8 ml of $PCl_3$ (0.432 mol). After an additional 5 hours at 70°C, the product was hydrolyzed with 300 ml of $H_2O$. Filtration with activated carbon at the boiling point yielded a clear solution from which the N-methylpyrrolidone-5,5-diphosphonic acid was precipitated with ethanol and acetone. Crude yield 4.2 gm (7% of the theory).

The N-methyl-pyrrolidone-5,5-diphosphonic acid was obtained after drying at 50°C as a monohydrate with a molecular weight of 279 (calc. 277.1). After drying at 80°C in the vacuum oven, the anhydrous compound was obtained with a molecular weight of 259 (calc. 259.1).

Analysis: Calculated: 23.18%, C; 4.28%, H; 5.41%, N; 23.91%, P. Found: 22.90, C; 4.16, H; 5.45, N; 23.12, P.

The compound shows in the IR-spectrum a strong $\nu$ CO band at 1650 cm$^{-1}$, M.P. above 270°C with decomposition.

EXAMPLE 3

N-ethyl-pyrrolidone-5,5-diphosphonic acid

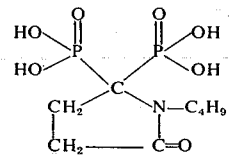

a. 88.5 gm of 1-ethyl-2-hydroxy-2-oxo-3-ethylamino-3-phosphonyl-6-oxo-1-aza-2-phospha-cyclohexane (0.295 mol) were boiled with 147.5 gm of a 40% NaOH solution (1.475 mol) for a length of time until no further ethylamine escaped. Then the product was filtered with activated carbon and the sodium salt of N-ethyl-pyrrolidone-5,5-diphosphonic acid was precipitated with ethanol and acetone. The oily substance was again dissolved in $H_2O$ and passed through a cation exchanger in the hydrogen cycle, and the N-ethyl-pyrrolidone-5,5-diphosphonic acid was isolated from the extract with ethanol and acetone. Yield 79 gm (90% of the theory).

b. 43.0 gm of succinic acid bisethylamide (0.25 mol) were melted with 82 gm of $H_3PO_3$ (1.0 mol) at 70°C. To the melt, 88 ml of $PCl_3$ (1.0 mol) were slowly added in drops and the mixture was left standing for 5 hours at 70°C. Then the mixture was hydrolyzed with 250 ml of $H_2O$ and filtered with activated carbon. The filtrate was mixed with 0.5 liter of 6N NaOH solution and heated so long until no further ethylamine passed over. The sodium salt of N-ethyl-pyrrolidone-5,5-diphosphonic acid was precipitated with ethanol/acetone, dissolved again in $H_2O$ and passed through a cation exchanger in the hydrogen cycle. The N-ethyl-pyrrolidone-5,5-diphosphonic acid was precipitated from the extract with ethanol and acetone. Yield 16.5 gm (22% of the theory). After drying at 50°C, the substance was obtained as a monohydrate with a molecular weight of 292 (calc. 291.1).

Analysis: Calculated: 24.75%, C; 5.19%, H; 21.28%, P. Found: 24.79, C; 5.06, H; 21.08, P.

After drying in the vacuum oven at 80°C, the anhydrous compound was obtained with a molecular weight of 276 (calc. 273.1).

In the IR-spectrum the substance shows a strong $\lambda$ CO band at 1640 cm$^{-1}$, M.P. 250°C.

EXAMPLE 4

N-butyl-pyrrolidone-5,5-diphosphonic acid

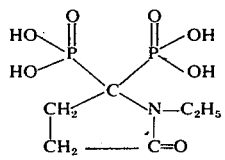

40 gm of 1-butyl-2-hydroxy-2-oxo-3-butylamino-3-phosphonyl-6-oxo-1-aza-2-phospha-cyclohexane (0.112 mol) were boiled with 400 ml of 2N NaOH solution for a length of time until no further butylamine escaped. Then the mixture was filtered with activated carbon and the sodium salt of N-butylpyrrolidone-5,5-diphosphonic acid was isolated with ethanol/acetone. The oily substrate was dissolved in water and passed through a cation exchanger in the hydrogen cycle. The N-butyl-pyrrolidone-5,5-diphosphonic acid was isolated from the concentrated extract with ethanol and acetone. Yield 23 gm (58% of the theory).

After drying at 50°C, the compound was obtained as a monohydrate.

The molecular weight was determined titrimetrically as 321 (calc. 319.2).

Analysis: Calculated: 30.10%, C; 6.00%, H; 4.39%, N; 19.41%, P. Found: 30.02, C; 5.66, H; 4.27, N; 18.64, P.

After drying at 80°C in a vacuum oven, the anhydrous compound was obtained with a molecular weight of 303 (calc. 301.2) The compound shows in the IR-spectrum a strong $\lambda$ CO band at 1660 cm$^{-1}$, M.P. over 240°C with decomposition.

EXAMPLE 5

Preparation of Salts a. 25.9 gm of N-methyl-pyrrolidone-5,5-diphosphonic acid were dissolved in 100 ml of water and mixed with 100 ml of a 4N lithium hydroxide solution. On addition of 300 ml of ethanol, the tetralithium salt of N-methyl-pyrrolidone-5,5-diphosphonic acid was precipitated.

b. 27.31 gm of N-ethyl-pyrrolidone-5,5-diphosphonic acid were dissolved in 100 ml of water and mixed with 100 ml of a 2N $NH_4OH$ solution. On addition of 300 ml of ethanol, the di-ammonium salt of N-ethyl-pyrrolidone-5,5-diphosphonic acid was precipitated.

c. 24.5 gm of pyrrolidone-5,5-diphosphonic acid (0.1 mol) were dissolved in 100 ml of water. To this solution, a solution of 13.6 gm of $ZnCl_2$ (0.1 mol)

dissolved in 50 ml of water was added. The precipitation of the zinc salt of pyrrolidone-5,5-diphosphonic acid was completed by the addition of 300 ml of ethanol.

d. The magnesium salt of pyrrolidone-5,5-diphosphonic acid was obtaind by replacing the $ZnCl_2$ by 9.4 gm of $MgCl_2$ (0.1 mol) using the same procedure as described under (c).

EXAMPLE 6

Sequestration of calcium

In the investigation of the sequestration of calcium, a modified Hampshire test was employed and worked as follows:

1 gm of the sequestering agent was dissolved in 50 ml of $H_2O$, adjusted with NaOH to a pH of 11. 50 ml of a $Ca^{++}$ solution (1470 mg of $CaCl_2.2H_2O/l$) were mixed with 100 ml of a sodium carbonate solution (7.15 gm $NaCO_3.10H_2O/l$). Then the solution of the sequestering agent was added in drops from a burette until the calcium carbonate precipitate was redissolved. The values have been reported in Table I. For the sake of simplicity, only the value for the various substituents for R according to Formula I are indicated in the left column of the Table.

TABLE I

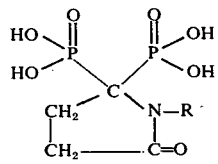

R = H or alkyl having 1 to 6 carbon atoms.

| Compound R | Consumption of Sequestering Agent Solution (ml) | mg $CaCO_3$ Sequestered per gm of Compound |
|---|---|---|
| H | 2.9 | 865 |
| $CH_3$ | 2.6 | 960 |
| $C_2H_5$ | 2.5 | 1000 |
| $C_4H_9$ | 2.9 | 865 |

Practically identical results were obtained if, instead of the acids, the corresponding sodium, potassium or ammonium salts were employed.

EXAMPLE 7

Threshold Effect

The prevention of the precipitation of poorly soluble calcium compounds by substoichiometric amounts of a sequestering agent was determined with the Hampshire test at room temperature. The procedure was as follows:

50 mg of the sequestering agent were dissolved in 10 ml of $H_2O$ (standardized with NaOH to pH 11) and mixed with 100 ml of a sodium carbonate solution (14.3 gm of $NaCO_3.10H_2O/l$). Then sufficient of a calcium solution (36.8 gm of $CaCl_2.2H_2O/l$) was added in drops from a burette until a permanent cloudiness was just formed. Table II reports the results of these tests. For an explanation of the data in the left-hand column of the Table, see Example 6.

TABLE II

| Substance R | Consumption of Ca Solution (ml) | Mg $CaCO_3$ | mg $CaCO_3$ Sequestered per gm of Compound |
|---|---|---|---|
| H | 2.1 | 52.5 | 1050 |
| $CH_3$ | 2.8 | 70.0 | 1400 |
| $C_2H_5$ | 3.3 | 82.5 | 1650 |
| $C_4H_9$ | 2.2 | 55.0 | 1100 |

Practically identical results are obtained if, instead of the acids, the corresponding sodium, potassium or ammonium salts were employed.

EXAMPLE 8

Delay of setting of Gypsum

Gypsum materials in the form of plaster, plaster of Paris, or in mixture with aggregates, like limestone, sand, perlite or cellulose, set relatively fast, so that rapid processing must take place. A delay of the setting time can be achieved with the addition of the above-described phosphonic acids, and the processing of the gypsum materials can thus be considerably facilitated.

In the following tests, each of the various phosphonic acids of the invention was added to the water before the gypsum was mixed. However, water-soluble salts of the phosphonic acids, particularly the lithium, sodium, potassium and ammonium salts can also be mixed instead with the gypsum or added shortly after the mixing of the gypsum material together with the water. Specifically the following setting values were found and reported in Table III, using in each test 20.0 gm of gypsum and 9 ml of $H_2O$. The setting time is the time interval in which the gypsm was spreadable and easy to handle.

For the explanation of the data in the left column of Table III, see Example 6.

TABLE III

| Substance R | Amount (mg) | Setting Time (min.) |
|---|---|---|
| — | — | 15 |
| H | 45 | 160 |
| $CH_3$ | 45 | 140 |
| $C_2H_5$ | 45 | 120 |
| $C_4H_9$ | 45 | 110 |

Comparable results are obtained by using the corresponding magnesium and zinc salts.

EXAMPLE 9

Pharmaceutical Application a. Calcium phosphate dissolution in vitro

Essential tests for the effectiveness of the compounds in physiological systems are in vitro tests for the dissolving of freshly precipitated $CaHPO_4$ at a pH of 7.4 The "$CaHPO_4$ test" was carried out as follows:

By combining 25 ml of a phosphate solution (1.38 gm of $NaH_2PO_4.H_2O/l$, standardized to a pH of 7.4) and 25 ml of a calcium solution (1.47 gm of $CaCl_2.2H_2O/l$, standardized to a pH of 7.4), a precipitate of $CaHPO_4$ was produced. Thereafter, so much of a solution of the sequestering agent (at a concentration of 10 mg/ml) was added dropwise from a burette that a clear solution was obtained after standing for 1 hour.

The results are compiled in the following Table IV. The explanation of the data in the left column is to be found in Example 6.

TABLE IV

| Substance R | Dissolution of CaHPO$_4$ Precipitation Consumption | |
|---|---|---|
| | Sequestering Agent Solution (ml) | mg CaHPO$_4$ dissolved gm Sequestering Agent |
| H | 3.8 | 900 |
| CH$_3$ | 3.8 | 900 |
| C$_2$H$_5$ | 4.4 | 775 |
| C$_4$H$_9$ | 4.8 | 710 | b. Prevention of hardening of the aorta in rats

The effectiveness of the pyrrolidone-5,5-diphosphonic acids of the present invention in preventing abnormal calcium deposits in vivo in rats can be demonstrated as follows.

This test was based on the observation that high doses of vitamin D$_3$ causes a considerable hardening of the aorta in rats. 30 Female rats weighing 150 to 200 gm each were divided into three groups of 10 animals each. They received during the test period a normal diet and tap water ad libitum. One group of 10 animals (control) received no further treatment. Another group of the animals received from the 3rd to the 7th day, 75,000 units of vitamin D$_3$ daily through a stomach sound. The third group likewise received from the 3rd to the 7th day, 75,000 units of vitamin D$_3$ daily through a stomach sound and, in addition, likewise orally, 10 mg per kg of one of the pyrrolidone-5,5-diphosphonic acids from the 1st to the 10th day. After 10 days the animals were sacrificed and their aortas prepared and dried for 12 hours at 105°C. After determination of the dry weight, the aortas were ashed; the residue was dissolved, and the calcium was determined by flame photometry. The treatment with all the pyrrolidone-5,5-diphosphonic acids mentioned above reduced the vitamin D$_3$ induced hardening of the aortas of rats considerably.

c. Apatite crystallization delay test in vitro

The effectiveness of the compounds according to the invention for the above-mentioned purposes was also demonstrated in vitro by a crystallization delay test.

Supersaturated solutions of Ca$^{++}$ and HPO$_4^{--}$ ions are relatively stable, but crystallize after the addition of an apatite nuclei according to the reaction

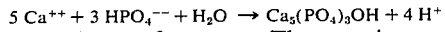
$$5\ Ca^{++} + 3\ HPO_4^{--} + H_2O \rightarrow Ca_5(PO_4)_3OH + 4\ H^+$$

with the release of protons. The reaction can, therefore, be readily observed by titration with a base at a constant pH.

400 ml Of 0.0008 molar KH$_2$PO$_4$ solution were mixed with 45 ml of a 0.012 molar CaCl$_2$ solution, and the clear solution was standaridized with KOH to a pH of 7.4, after being brought to a temperature of 35°C. After 30 minutes during which time the pH did not change, a suspension of 100 mg hydroxyl apatite in 50 ml of H$_2$O was added. The crystallization set in immediately and was followed by "pH-Stat" titration with 0.05 N KOH.

If a small amount of one of the pyrrolidone-5,5-diphosphonic acids of the invention was added to the solution before the apatite was added, the crystallization was greatly delayed.

The inhibition of the crystallization with 2 mg of pyrrolidone-5,5-diphosphonic acid is over 90% in a period of 8 hours, with 2 mg N-methyl-pyrrolidone-5,5-diphosphonic acid it is over 80% in a period of 8 hours.

EXAMPLE 10

Pharmaceutical Compositions

For the production of a pharmaceutical preparation in the form of a capsule, the known methods of preparation are followed to prepare capsules having a content per capsule as follows:

| | |
|---|---|
| Pyrrolidone-5,5-diphosphonic acid | 100 mg |
| Starch | 20 mg |
| Sodium laurylsulfate | 1 mg |

For the preparation of a tablet, the following recipe was utilized per tablet:

| | |
|---|---|
| N-methyl-pyrrolidone-5,5-diphosphonic acid | 50 mg |
| Lactose | 100 mg |
| Starch | 35 mg |
| Magnesium stearate | 2 mg |

EXAMPLE 11

Cosmetic Preparations

The following recipes are suitable as a basic formula for tooth pastes:

| | Parts by Weight |
|---|---|
| (a) Glycerin | 60.0 |
| Water | 13.5 |
| Sodium carboxymethyl-cellulose | 0.6 |
| Silicic acid xerogel | 20.0 |
| Sodium laurylsulfate | 2.0 |
| Essential oils | 1.0 |
| Sweetening agent | 0.4 |
| Pyrrolidone-5,5-diphosphonic acid | 2.5 |
| (b) Glycerin | 30.0 |
| Water | 18.5 |
| Sodium carboxymethyl-cellulose | 1.0 |
| Aluminum hydroxide | 44.0 |
| Sodium laurylsulfate | 1.0 |
| Pyrogenic silica | 1.5 |
| Essential oils | 1.5 |
| Sweetening agent | 0.5 |
| Pyrrolidone-5,5-diphosphonic acid | 2.0 |

Suitable as a basic formation for mouthwashes is the following recipe:

| | Parts by Weight |
|---|---|
| Ethyl alcohol | 19.5 |
| Glycerin | 7.5 |
| Water | 70.0 |
| Essential oils | 0.2 |
| Sodium laurylsulfate | 0.1 |
| Antiseptic (chlorothymol) | 0.1 |
| Sweetening agent | 0.1 |
| Pyrrolidone-5,5-diphosphonic acid | 2.5 |

Instead of pyrrolidone-5,5-disphosphonic acid, the corresponding amounts of N-alkylpyrrolidone-5,5-diphosphonic acids (alkyl radical with 1 to 6 carbon atoms) can also be employed.

By regular use of the mouthwashes and/or toothpastes containing the above-mentioned pyrrolidone-5,5-diphosphonic acids, the formation of tartar could be considerably reduced. The formation of hard compact plaque on the teeth was to a great extent prevented.

The preceding specific embodiments are illustrative of the pracitce of the invention. It is to be understood, however, that other expedients known to those skilled in the art or discussed herein may be employed without departing from the spirit of the invention or the scope of the appended claims.

We claim:

1. Pyrrolidone-5,5-diphosphonic acid compound of the formula

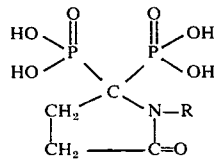

wherein R is a member selected from the group consisting of hydrogen, alkyl having from 1 to 6 arbon atoms, and non-toxic, pharmaceutically acceptable water-soluble salt thereof.

2. The pyrrolidone-5,5-diphosphonic acid compound of claim 1 wherein R is hydrogen.

3. The pyrrolidone-5,5-diphosphonic acid compound of claim 1 wherein R is methyl.

4. The pyrrolidone-5,5-diphosphonic acid compound of claim 1 wherein R is ethyl.

5. The pyrrolidone-5.5-diphosphonic acid compound of claim 1 wherein R is butyl.

6. The pyrrolidone-5,5-diphosphonic acid compound of claim 1, wherein said non-toxic, pharamaceutically acceptable watersoluble salt is a member selected from the group consisting of alkali metal, ammonium, zinc and magnesium.

7. The pyrrolidone-5,5-diphosphonic acid compound of claim 6, wherein said water-soluble salt reacts substantially neutral with a pH of 5 to 9 in an aqueous solution.

8. A process for the production of the pyrrolidone-5,5-diphosphonic acid compound of claim 1 which consists essentially of the steps reacting at a temperature between 50°C and 120°C succinic compound of the formula $$X - CH_2 - CH_2 - X$$

wherein X is a member selected from the group consisting of —CN, —CONH$_2$ and —CONHR′, where R′ is alkyl having 1 to 6 carbon atoms, with at least the stoichiometric amount of a phosphorus reactant selected from the group consisting of a phosphorus trihalide and a mixture of a phosphorus trihalide and phosphorous acid, subjecting the resulting reaction product to an alkaline hydrolysis by the action of an aqueous stong mineral base, and recovering said pyrrolidone-5,5-diphosphonic acid compound.

9. A process for the production of the pyrrolidone-5,5-diphosphonic acid compound of claim 1 which consists essentially of the steps of reaching at a temperature between 50°C and 120°C succinic compound selected from the group consisting of a compound of the formula

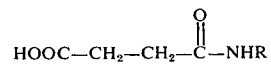

and a compound of the formula

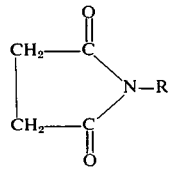

wherein R is a member selected from the group consisting of hydrogen and alkyl having 1 to 6 carbon atoms, with at least the stoichiometric amount of a phosphorus reactant selected from the group consisting of a phosphorus trihalide and a mixture of a phosphorus trihalide and phosphorus acid, subjecting the resulting reaction product to an aqueous hydrolysis by the action of an aqueous media selected from the group consisting of water at an elevated temperature and an aqueous strong mineral base, and recovering said pyrrolidone-5,5-diphosphonic acid compound.

* * * * *